United States Patent
Grandhe

(10) Patent No.: US 7,603,179 B1
(45) Date of Patent: Oct. 13, 2009

(54) SYSTEM AND METHOD FOR LEAD FIXATION

(75) Inventor: Sarvani Grandhe, Glendale, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 356 days.

(21) Appl. No.: 10/941,220

(22) Filed: Sep. 15, 2004

Related U.S. Application Data

(60) Provisional application No. 60/503,518, filed on Sep. 16, 2003.

(51) Int. Cl.
*A61N 1/18* (2006.01)
(52) U.S. Cl. ...................... 607/122; 607/116
(58) Field of Classification Search ......... 607/115–119, 607/122–124, 129, 133
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,822,708 A | 7/1974 | Zilber | |
| 4,282,886 A | 8/1981 | King | |
| 4,338,945 A | 7/1982 | Kosugi et al. | |
| 4,379,462 A | 4/1983 | Borkan et al. | |
| 4,418,697 A | 12/1983 | Tama | |
| 4,519,403 A | 5/1985 | Dickhudt | |
| 5,121,754 A | 6/1992 | Mullett | |
| 5,417,719 A | 5/1995 | Hull et al. | |
| 5,476,500 A * | 12/1995 | Fain et al. | 607/126 |
| 5,501,703 A | 3/1996 | Holsheimer et al. | |
| 5,578,067 A * | 11/1996 | Ekwall et al. | 607/122 |
| 5,733,322 A | 3/1998 | Starkebaum | |
| 5,759,202 A * | 6/1998 | Schroeppel | 607/126 |
| 5,824,030 A * | 10/1998 | Yang et al. | 607/122 |
| 5,931,864 A * | 8/1999 | Chastain et al. | 607/128 |
| 6,078,840 A | 6/2000 | Stokes | |
| H1905 H * | 10/2000 | Hill | 607/122 |
| 6,304,786 B1 * | 10/2001 | Heil et al. | 607/126 |
| 6,330,481 B1 | 12/2001 | Van Wijk et al. | |
| 6,405,091 B1 * | 6/2002 | Vachon et al. | 607/120 |
| 6,473,654 B1 | 10/2002 | Chinn | |
| 6,968,238 B1 * | 11/2005 | Kuzma | 607/137 |
| 7,212,867 B2 * | 5/2007 | Van Venrooij et al. | 607/116 |
| 2002/0156513 A1 * | 10/2002 | Borkan | 607/117 |
| 2006/0129217 A1 * | 6/2006 | Krishnan | 607/116 |

OTHER PUBLICATIONS

Whitehurst, et al.; U.S. Appl. No. 10/146,332, filed May 15, 2002; entitled "Fixation Device for Implantable Microdevices".
Thacker, et al.; U.S. Appl. No. 10/155,146, filed May 24, 2002; entitled "Neural Stimulation Lead Fixation".

* cited by examiner

*Primary Examiner*—Carl H. Layno
*Assistant Examiner*—Tammie K. Heller
(74) *Attorney, Agent, or Firm*—Darby & Darby PC

(57) ABSTRACT

A medical lead includes a pitted, grooved or threaded electrode array tip and a flexible tube or sheath encompassing the electrode array located near the lead tip. In some embodiments, the electrode array adheres to tissue, the tube or sheath adheres to the electrode array at the distal end of the electrode array or the tube or sheath adheres to tissue at the proximal end of the tube or sheath. Embodiments of the tube or sheath may be made from biodegradable material and can include electrode windows spaced along the tube or sheath corresponding to placement of electrode contacts of the electrode array.

23 Claims, 4 Drawing Sheets

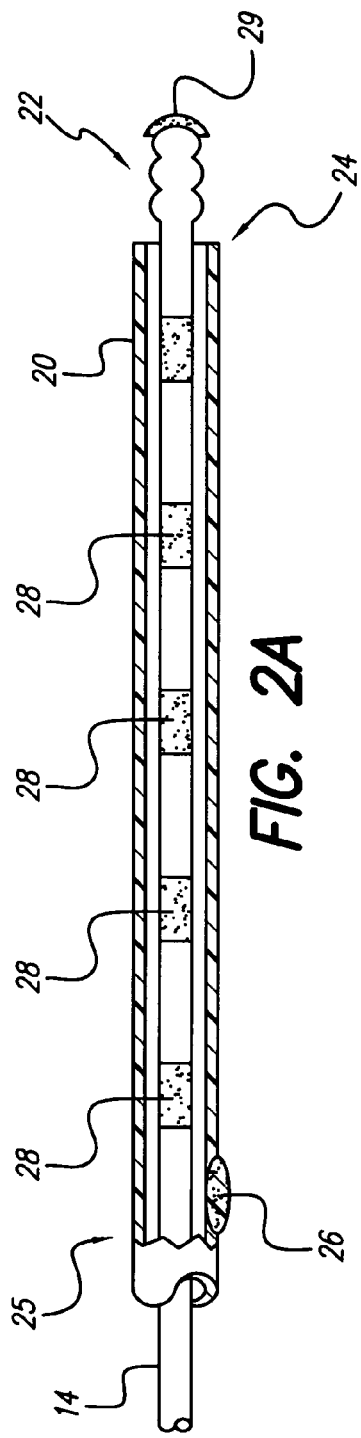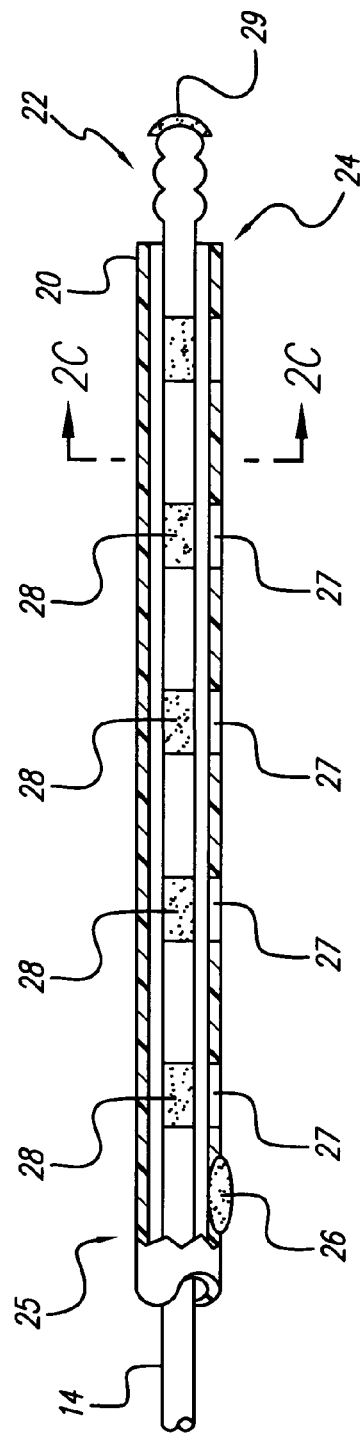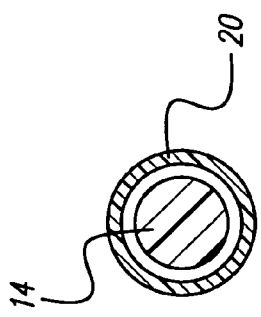

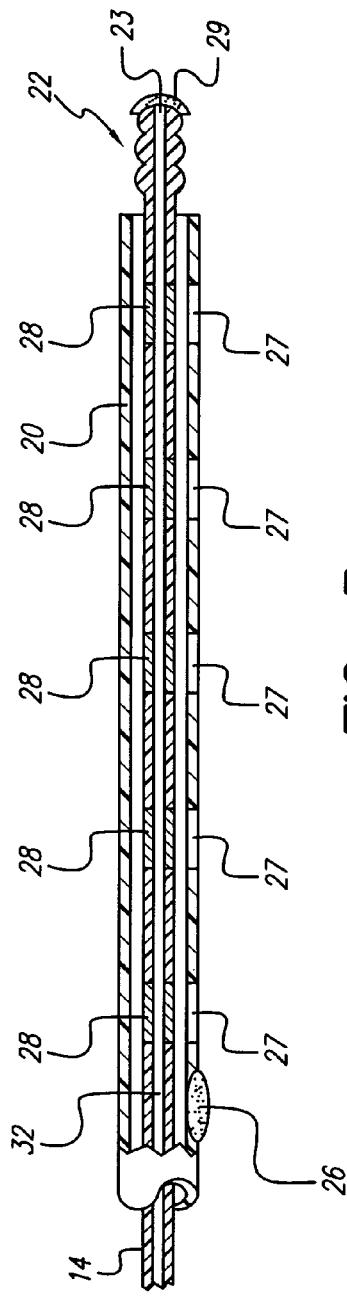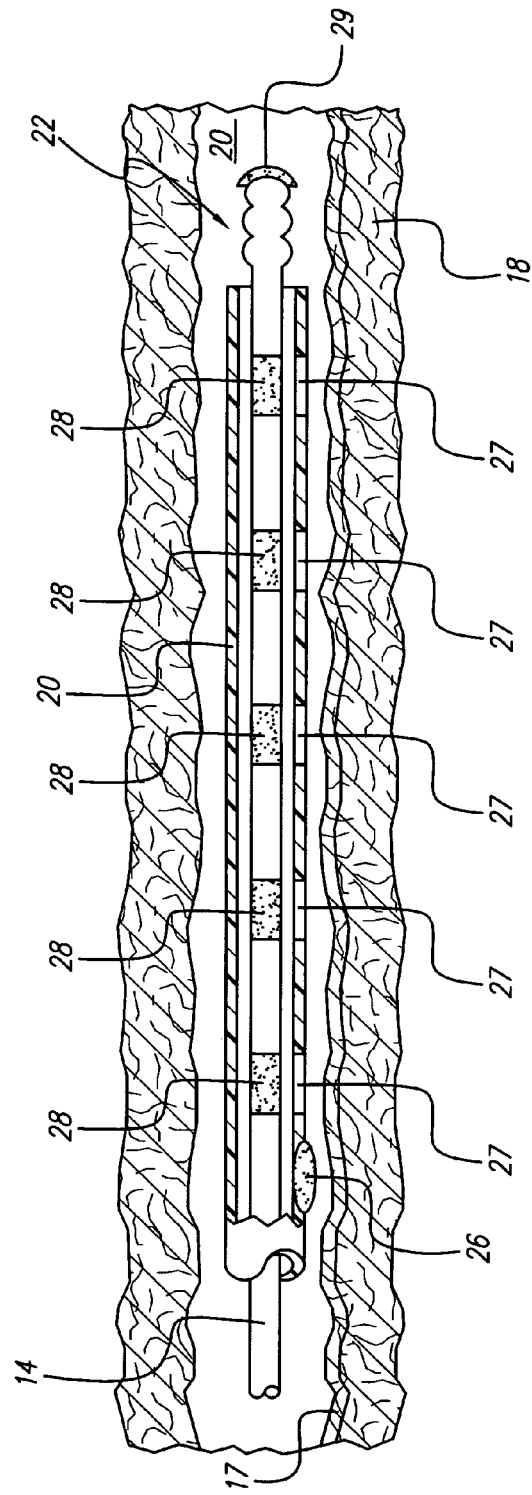

SYSTEM AND METHOD FOR LEAD FIXATION

The present application claims the benefit of U.S. Provisional Patent Application Ser. No. 60/503,518, filed 16 Sep. 2003, which application is herein incorporated by reference in its entirety.

BACKGROUND OF THE INVENTION

The present invention relates to medical stimulation systems, e.g., a spinal cord stimulation system. More particularly, the invention relates to medical stimulation leads that include lead fixation means, i.e., ways to ensure that the lead, once implanted, does not move away from its desired implant location.

Spinal cord stimulation (SCS) is a well accepted clinical method for reducing pain in certain populations of patients. SCS systems typically include an implanted pulse generator, lead wires, and electrodes connected to the lead wires. The pulse generator generates electrical pulses that are delivered to the dorsal column fibers within the spinal cord through the electrodes which are implanted along the dura of the spinal cord. In a typical application, the attached lead wires exit the spinal cord and are tunneled around the torso of the patient to a subcutaneous pocket where the pulse generator is implanted.

When an electrical pulse or sequence of pulses is applied to a selected electrode or combination of electrodes, the patient typically experiences a "paresthesia" (usually manifested as a mild tingling sensation) that is therapeutic, i.e., relieves the pain or other discomfort that the patient is experiencing.

Spinal cord and other stimulation systems are known in the art. For example, in U.S. Pat. No. 3,646,940, there is disclosed an implantable electronic stimulator that provides timed sequenced electrical impulses to a plurality of electrodes so that only one electrode has a voltage applied to it at any given time. Thus, the electrical stimuli provided by the apparatus taught in the '940 patent comprise sequential or non-overlapping stimuli.

In U.S. Pat. No. 3,724,467, an electrode implant is disclosed for the neuro-stimulation of the spinal cord. A relatively thin and flexible strip of physiologically inert plastic is provided with a plurality of electrodes formed thereon. The electrodes are connected by leads to an RF receiver, which is also implanted, and which is controlled by an external controller. The implanted RF receiver has no power storage means and must be coupled to the external controller in order for neurostimulation to occur.

In U.S. Pat. No. 3,822,708, another type of electrical spinal cord stimulating device is shown. The device has five aligned electrodes which are positioned longitudinally on the spinal cord and transversely to the nerves entering the spinal cord. Current pulses applied to the electrodes are said to block sensed intractable pain, while allowing passage of other sensations. The stimulation pulses applied to the electrodes are approximately 250 microseconds in width with a repetition rate of from 5 to 200 pulses per second. A patient-operable switch allows the patient to change which electrodes are activated, i.e., which electrodes receive the current stimulus, so that the area between the activated electrodes on the spinal cord can be adjusted, as required, to better block the pain.

Other representative patents that show spinal cord stimulation systems or electrodes include U.S. Pat. Nos. 4,338,945; 4,379,462; 4,519,403; 5,121,754; 5,417,719 and 5,501,703. Each patent is incorporated herein by reference.

U.S. Pat. No. 5,733,322, also incorporated herein by reference, discloses a positive fixation percutaneous epidural neuro-stimulation lead that utilizes an extension that extends distally beyond the most distal electrode. The extension is held in place by contact with both the dura and spinal canal wall so that lateral lead migration of the electrodes is minimized. Other electrode fixation techniques are taught, e.g., in U.S. Pat. No. 4,418,697, which describes an adhesive (putty) to fixate electrodes to the skin; and in U.S. Pat. No. 4,282,886, which describes an adhesive adapted to attach an electrode to the epicardium. Both the '697 and the '886 patents are likewise incorporated herein by reference.

On a daily basis, patients change posture during sitting, bending, sleeping, walking or other activities that cause implanted neural stimulation leads to flex and move. Disadvantageously, when a neural stimulation lead chronically or temporarily moves, it can affect the treatment results. For example, an SCS lead that moves up, down or rotates to the side of the spinal cord can result in therapy no longer being adequate to attain the desired paresthesia, thereby rendering the SCS system incapable of performing its intended function. When a lead moves temporarily, the lead movement may thereafter require an adjustment to the delivered stimulation energy, e.g., a reduction of the stimulation output or an increase of the stimulation output. In some instances such adjustment of the stimulation energy may not be possible, thereby rendering the SCS system less effective or even ineffective for its intended purpose. In the worst case scenario, the patient must submit to a surgical procedure to manually adjust the location of the lead in order to regain effective SCS system operation.

Thus, it is seen that maintaining the correct lead position is critical, and an undesirable movement of the lead can render the SCS, or other neural stimulation system, ineffective and useless. What is needed are lead designs that (1) chronically fixates the lead to its desired location, e.g., to the dura in the case of an SCS system; and (2) fixates the lead in a manner that provides adequate lead flexibility to accommodate postural changes.

BRIEF SUMMARY OF THE PREFERRED EMBODIMENTS

The present invention addresses the above and other needs by providing lead designs that permit improved fixation to the dura in a manner that also permits adequate flexibility to the lead to accommodate postural changes.

An electrode array of a lead is enclosed in a flexible tubing or sheath made of biocompatible material. The electrode array and sheath are inserted adjacent to the dura of the spine. The tip of the electrode array can be pitted, grooved or threaded in a manner that facilitates maturation of scar tissue over time near the electrode array tip. Scar maturation serves to fix the electrode array to the dura, thus minimizing lead migration. Nevertheless, the pitted, grooved, or threaded construction of the tip of the electrode array permits the lead to be easily explanted. A twisting action that applies rotational force or torque to the body of the lead during explantation can easily detach the grooved or threaded electrode array located at the distal tip of a lead from the surrounding scar tissue.

The distal end of the flexible tubing may adhere to and enclose the electrode array just adjacent to the electrode array tip. The proximal end of the flexible tubing can adhere to the dura by a heat sensitive adhesive or other bonding agent that may be biodegradable. With postural changes, such as bending and movement of the spinal cord, the sheath or flexible tubing enclosing the electrode array flexes in accommodation. The flex of the tubing helps to keep the electrode array in position and minimizes the lateral movement of the electrode array along the spinal cord.

In one embodiment of the method, in accordance with the present invention, a flexible tubing or sheath is left behind during explantation of the electrode array originally inside the tubing or sheath. The flexible tubing or sheath, thus remaining, may then be used to introduce a new lead into the same location as the previous lead.

In a further embodiment of the invention, the flexible tubing or sheath may include windows or openings along the body of the tubing or sheath. These openings can be spaced relative to the electrode contacts of the electrode array, thereby permitting more focused stimulation energy and maximal electrical contact between the electrode contacts and adjacent tissue.

In another embodiment, the biocompatible material of the flexible tube or sheath is biodegradable. When the lead is explanted, the material enclosing the lead is preferably capable of dissolving or otherwise disassociating over time. This aspect of the present invention is particularly helpful for short clinical trial periods when the lead will not remain in the patient for a long period of time.

In yet a further embodiment, the tip of the electrode array may be coated with an adhesive that may be biodegradable and that permits the tip to further fixate itself to the dura during implantation. Biodegradable adhesive may be injected through a lumen in the lead body to the end of the electrode array. The adhesive exudes from the electrode array tip to fix the electrode array to the dura.

The lead designs with fixation sheath thus permits lead fixation to the dura of the spine in a manner that is flexible, non-migrational, and explantable. In addition, the lead designs permit focused stimulation energy and maximum contact between the electrode contacts and adjacent tissue and, moreover, can provide in certain embodiments, same-location implantation of new leads after explantation of old leads.

BRIEF DESCRIPTION OF THE DRAWINGS

The above and other aspects of the present invention will be more apparent from the following more particular description thereof, presented in conjunction with the following drawings wherein:

FIG. 2A shows, in accordance with the present invention, a side cut-away view of one embodiment of a lead with fixation device in the form of a sheath;

FIG. 2B shows, in accordance with the present invention, a side, cut-away view of another embodiment of a lead and sheath, wherein the sheath has openings or electrode windows to expose the electrodes;

FIG. 2C shows a cross-sectional view of the lead and sheath shown in FIG. 2B along line 2C-2C.

FIG. 3 shows, in accordance with the present invention, a side cut-away view of yet another embodiment of an electrode array (lead) and sheath, wherein the electrode array has a lumen through its core that exits at the tip of the lead;

FIG. 4 shows a side cut-away view of the electrode array and sheath of FIG. 2B implanted adjacent to the spine;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

It should be noted that the present invention is directed to the fixation of implantable leads, such as neural stimulation leads or cardiac leads, and more particularly to the fixation of electrodes or electrode arrays, attached to neural stimulation leads or cardiac leads so that such electrodes or electrode arrays remain in a desired position relative to the tissue that is to be stimulated. For purposes of the present application, the terms "electrode array" and "electrode" may be used interchangeably, unless the context clearly indicates otherwise. That is, while a purpose of the invention is to fix the electrodes relative to the tissue to be stimulated, in describing such purpose, other terminology may be used, such as fixing the electrode array.

It should further be noted that the principles and teachings of the invention may be used with any kind of neural stimulation lead, particularly those that are implanted within a tissue cavity. Thus, while the invention is described in terms of a spinal cord stimulation (SCS) lead adapted for implantation in the epidural space next to the spine, it will be understood that such description is only exemplary and not limiting and that the scope of the invention will be determined by the claims.

Figure 1:
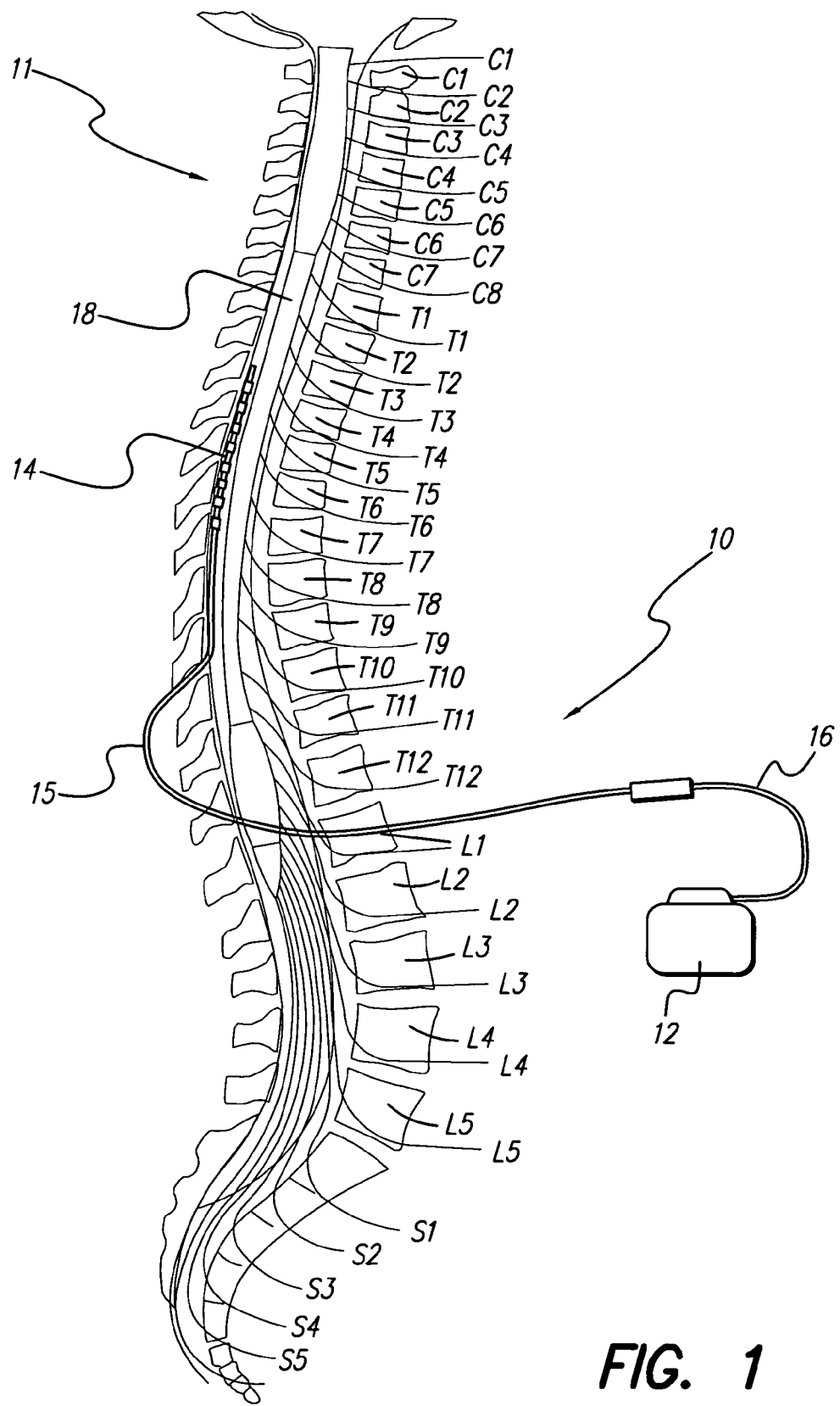
FIG. 1 illustrates a representative spinal cord stimulation system implanted in a patient.

FIG. 1 shows a representative SCS system 10 implanted in a patient 11. The SCS system 10 is used typically to treat chronic pain by applying electrical stimulation pulses to selected locations along the spine. The SCS system 10 includes an Implantable Pulse Generator (IPG) 12 that generates electrical stimulation pulses used for stimulation. An electrode array 14 at or near the distal end of an implanted stimulation lead 15 is inserted into the epidural space next to the spinal cord 18. As required, depending upon the location where the IPG 12 is implanted, a lead extension 16 may be used to connect the lead 15, and hence the electrode array 14, to the IPG 12. The electrical stimulation provided by the IPG 12, when properly performed, has the effect of masking sensed pain. The present invention relates to the electrode array 14 and the manner used to fix the location of the electrode array 14 relative to the spinal cord 18.

FIG. 2A shows one embodiment of the electrode array 14 and sheath 20, in accordance with the present invention. The sheath 20 has no openings and therefore the electrode contacts 28 of the electrode array 14 must be able to stimulate target tissue through the material of the sheath. The sheath 20 may therefore be relatively electrically porous to allow current to pass through the sheath 20. The electrode array 14 and sheath 20 can be injected or inserted into the epidural space next to the spinal cord 18 (see FIG. 1).

FIG. 2B shows another embodiment of the electrode array 14 with sheath 20, in accordance with the present invention. FIG. 2C shows a cross-sectional view of the electrode array 14 and sheath 20 along line 2C-2C of FIG. 2B. The flexible tubing or sheath 20 may be made of a natural or synthetic biocompatible material, such as silicone, bioactive polymers (polypeptides), polyurethane, polyethylene, polysulfone, polypropylene, teflon, silk, nylon, or other biocompatible polymers, textiles, or materials and any mixtures thereof.

The flexible tubing or sheath 20 can have openings or electrode windows 27 along the body of the tubing or sheath 20, which electrode windows expose the electrode contacts 28 so that the electrode contacts are adjacent to surrounding body tissue or fluid. These openings 27 are placed to correspond with the placed locations of electrode contacts 28 of the electrode array 14, thereby permitting more focused stimulation energy and maximal electrical contact between the contacts 28 and adjacent tissue. Both embodiments of the electrode array 14 and sheath 20 shown in FIGS. 2A and 2B can have a type of adhesive 29 applied to the electrode array tip 22 (which is also the distal tip of the lead 15 shown in FIG. 1). The adhesive 29 may be, among others, cyanoacrylate, fibrin, reconstituted collagen, polyethylene glycol, polyacrylamide or any other suitable adhesive, including a biodegradable adhesive. The adhesive 29 may help to fix the electrode array 14 to the tissue until scar tissue can form over the electrode array 14 and the sheath 20.

The electrode array tip 22 can be configured to facilitate fixation. The tip 22 of the electrode array may be grooved or threaded in a manner that facilitates maturation of scar tissue over time at the tip 22. FIGS. 2A and 2B, for example, show a tip 22 that has small grooves to allow scar tissue to form around the grooves and to provide anchoring. Other forms of the tip 22 are also possible and within the scope of the invention.

Figure 5:
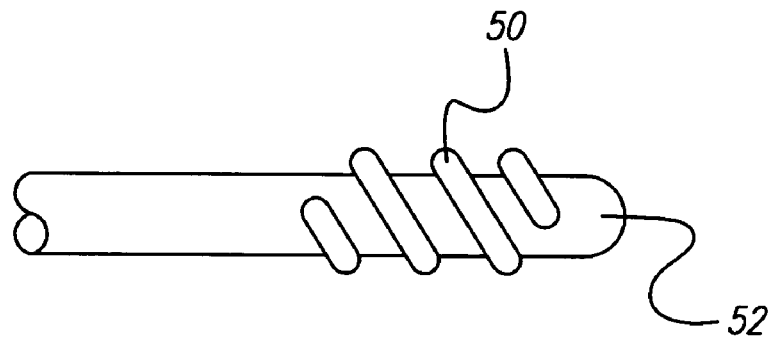
FIG. 5 depicts a side view of a threaded electrode array tip in accordance with the present invention.

FIG. 5, for example, shows a side view of an embodiment of a threaded electrode array tip, in accordance with the present invention, showing threads 50 on the tip 52 of an electrode array. The threads 50 may be made of the same biocompatible material as the lead or the threads 50 may be made of a different material. The threads 50 may be of various turns, size or spacing.

Figure 6:
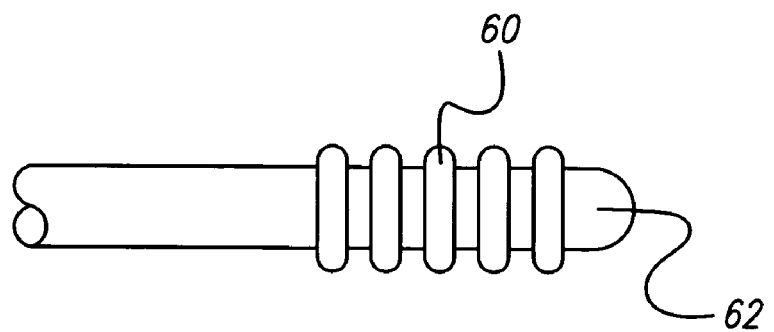
FIG. 6 depicts a side view of a grooved electrode array tip in accordance with the present invention.

FIG. 6 shows a side view of an embodiment of a grooved electrode array tip, in accordance with the present invention, showing grooves 60 on the tip 62 of the electrode array. The grooves 60 may be made of the same biocompatible material as the lead. The grooves 60 may be of various number, size and spacing.

Figure 7:
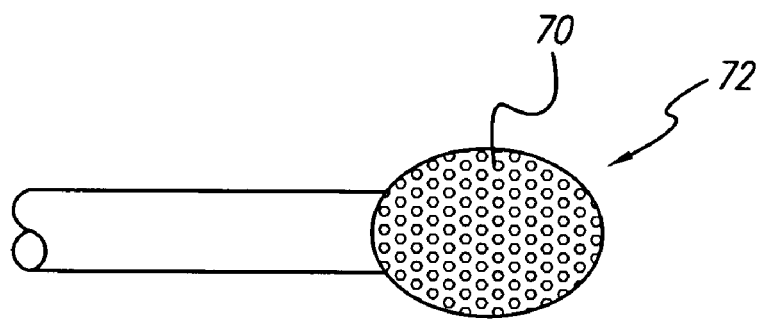
FIG. 7 depicts a side view of a pitted electrode array tip in accordance with the present invention.

FIG. 7 shows a side view of an embodiment of a pitted electrode array tip, in accordance with the present invention, showing pits 70 on a bulbed tip 72 of the electrode array. In other embodiments, a pitted tip may be any exterior shape, including threads and grooves in which the pits reside within the threads or grooves. The individual pits 70 may be of various number, size, spacing or dimension. The pits 70 may be embedded within the surface of the electrode array tip 72 in a manner similar to the indentations of a golf ball. The pits 70 may be varied in their dimensions, i.e., depth, volume, width, diameter or spacing. When a pitted electrode array tip 72 is used, it can facilitate the maturation of scar tissue over time around the electrode array tip 22.

Returning again to FIGS. 2A and 2B, regardless of the specific configuration of fixation tip employed, scar maturation serves to fix the electrode array 14 in the epidural space of the spine, thus minimizing lead migration. Advantageously, although providing sufficient fixation when implanted, the grooved, threaded or pitted construction of the electrode array tip 22 permits the lead to be easily explanted, when desired. By twisting or rotating the lead 15, a surgeon can release the electrode array tip 22 from attachment to surrounding scar tissue and the electrode array tip 22 may be easily detached from the dura of the spine (or other body tissue).

The distal end 24 of the flexible tubing or sheath 20 encloses the electrode array 14 at the electrode array tip 22. In one embodiment, the distal end 24 of the flexible tubing 20 can adhere to the electrode array 14 just adjacent to the electrode array tip 22. The proximal end 25 of the flexible tubing may adhere to the dura by applying a heat sensitive adhesive 26 or some other bonding agent to the proximal end 25 of the tubing/sheath 20. The adhesive 26 may be biodegradable. With postural changes such as bending, the spinal cord 18 (see FIG. 1) moves and the sheath or flexible tubing 20 enclosing the electrode array 14 can flex accordingly. The flexion of the tubing 20 helps to keep the electrode array 14 in position and minimizes the lateral movement of the electrode array 14 along the spinal cord 18 (see FIG. 1).

Another embodiment of the flexible tube or sheath uses biodegradable material, such as biodegradable mesh. When the lead 15, as shown in FIG. 1, is explanted, the mesh enclosing the lead 15 is preferably capable of dissolving or otherwise disassociating over time. This embodiment is particularly helpful for short clinical trial periods where the lead will not remain in the patient for a long period of time. A biodegradable tube or sheath may also be used with a chronically or permanently implanted lead, where the biodegradable tube or sheath dissolves over a relatively long period of time.

In another embodiment, the electrode array tip 22 can be coated with an adhesive 29 that is biodegradable and that permits the electrode array tip to help fixate itself to the dura and surrounding tissue during and after implantation. When the lead 15 is explanted, the bond between the electrode array tip and the dura and surrounding tissue can be easily broken by twisting or rotating the lead 15.

FIG. 3 shows another embodiment of the invention, showing electrode array 14 with electrodes 28, sheath 20, which sheath has electrode windows 27. In this embodiment, a lumen 32 extends axially along the lead length through a central core of the lead 15 (FIG. 1) and exits at the distal electrode array tip (lead tip) 22 at opening 23. In this embodiment, adhesive 29, which may be biodegradable, can be introduced into the lumen 32 through some opening (not shown) at some part of the lead 15. The adhesive 20 can be pushed out or exuded through the tip opening 23 at the end of the electrode array tip 22. The adhesive 29 exuded from the tip opening 23 can cure and help to fix the electrode array 14 to the dura or some other target tissue. The adhesive 29 should have properties that allow it to be readily injected through the lumen 32 of the lead 15. Additionally, the adhesive 29 should have properties that cause it to adhere sufficiently to the dura 17 (see FIG. 4). When the lead 15 is explanted, the bond between the electrode array tip 22 and the dura and surrounding tissue can be easily broken by twisting or rotating the lead 15. The adhesive 29 may be, among others, cyanoacrylate, fibrin, reconstituted collagen, polyethylene glycol, polyacrylamide or any other suitable adhesive, including a biodegradable adhesive. The proximal end of the flexible tubing 20 may be adhered to the dura by applying a heat sensitive adhesive 26 or other bonding agent. Adhesive 26 may be the same type of adhesive already mentioned as adhesive 29 that may be used at the electrode array tip 22.

It is thus seen that various embodiments of the present invention include the use of an adhesive or adhesives to fix the electrode array 14 itself to the tissue. While the embodiment shown in FIG. 3 contemplates injecting the adhesive through the lumen 32 of the lead 15 (see FIG. 1), other techniques may be used, particularly for other types of lead and electrode configurations. In addition, the adhesives 29 and 26 may be placed before, during or after the implantation of the lead. The adhesives can be advantageously formulated to be gentle to the tissue and to ensure that the electrode array remains in the desired location and orientation. The adhesive may be made soft or hard, permanent or temporary, i.e., biodegradable. The adhesive may be a synthetic, e.g., cyanoacrylate or it may be a bonding agent that is natural to the body, e.g., fibrin glue.

FIG. 4 shows a side, cut-away view of the electrode array 14 of FIG. 2B having a sheath 20 with electrode windows 27, which are implanted in the epidural space 20 adjacent the spinal cord 18. As seen in FIG. 4, the electrode array 14 typically includes a multiplicity of spaced-apart electrode contacts 28. Such electrode contacts 28 may reside along one side of the array 14, or they may define bands that completely or partially encircle the body of the lead 15. Each electrode contact 28 is electrically connected to a respective wire (not shown) that is, in turn, connected to the IPG 12 (see FIG. 1). The optional adhesive 29 applied to the electrode array tip 22 can fix the body of the electrode array 14 to the body tissue. The adhesive 26 applied at the proximal end of the flexible tubing or sheath 20 can also help fix it to the dura 17 or other tissue. In this manner, the modified lead design of the present invention may be secured or fixed to the tissue of the spine in the epidural space 20 or other body tissue, thus permitting the electrode array 14 to maintain its location as the patient changes posture during normal daily activity.

An embodiment of a method, in accordance with the present invention, includes maintaining the location of flexible tubing or sheath 20 during explantation of a previously implanted electrode array 14. After the previously implanted electrode has been withdrawn or explanted, the sheath 20 may be left in place in the patient's body. The flexible tubing or sheath 20 remaining behind in a patient's body may then be used to implant a new lead in the same location of the epidural space of the spine as the previously implanted lead. This saves the physician time during implantation of a new lead and ensures accurate positioning of the new lead implantation.

In other embodiments, in accordance with the present invention, the proximal end 25 of the flexible tubing 20 may be marked, e.g., by radio-opaque markers or another form of marking to indicate a site of entry for implantation and to make this point easily visible to a physician during explantation. Preferably, in this embodiment, the flexible tubing or sheath 20 is made of a material that is strong enough to avoid collapse under the pressure of surrounding tissue once the electrode array 14 has been explanted.

While the invention herein disclosed has been described by means of specific embodiments and applications thereof, numerous modifications and variations could be made thereto by those skilled in the art without departing from the scope of the invention set forth in the claims.

What is claimed is:

1. An implantable medical lead comprising:
a lead body with a proximal end and a distal end;
an array comprising spaced-apart electrodes disposed along the distal end of the lead body;
a tip at the distal end of the lead body, wherein the tip includes adhesive configured and arranged for contacting tissue and adhering the lead to the tissue when the lead is implanted; and
a unitary, implantable sheath of flexible tubing disposed over at least a portion of the lead body and over at least a portion of each of two or more of the electrodes, wherein the sheath has biodegradable adhesive configured and arranged for contacting tissue and adhering the lead to the tissue when the lead is implanted.

2. The implantable medical lead of claim 1, wherein the adhesive on the tip is biodegradable.

3. The implantable medical lead of claim 1, wherein the tip includes at least one of pits, threads and grooves.

4. The implantable medical lead of claim 3, wherein at least a portion of the tip is threaded.

5. An implantable medical lead comprising:
a lead body with a proximal end and a distal end;
an array comprising spaced-apart electrodes disposed along the distal end of the lead body;
a tip at the distal end of the lead body, wherein the lead body has a lumen along the lead length, which lumen has a first opening at the tip and a second opening at another location of the lead body, wherein adhesive may be injected through the second opening and out through the first opening; and
a unitary, implantable sheath of flexible tubing disposed over at least a portion of the lead body and over at least a portion of each of two or more of the electrodes, wherein the sheath has biodegradable adhesive configured and arranged for contacting tissue and adhering the lead to the tissue when the lead is implanted.

6. The lead of claim 5, further comprising a biodegradable adhesive for injecting through the second opening and out through the first opening.

7. An implantable medical lead comprising:
a lead body with a proximal end and a distal end;
an array comprising spaced-apart electrodes disposed along the distal end of the lead body;
a tip at the distal end of the lead body; and
a unitary, implantable sheath of flexible tubing disposed over at least a portion of the lead body and over at least a portion of each of two or more of the electrodes, wherein the sheath has biodegradable adhesive configured and arranged for contacting tissue and adhering the lead to the tissue when the lead is implanted.

8. The lead of claim 7, wherein the biodegradable adhesive comprises tissue adhesive disposed at the proximal end of the flexible sheath.

9. The implantable medical lead of claim 7, wherein the sheath has electrode windows spaced along the sheath to expose at least one electrode contact of the electrode array.

10. An implantable medical lead comprising:
a lead body with a proximal end and a distal end;
an array comprising spaced-apart electrodes disposed along the distal end of the lead body;
a tip at the distal end of the lead body; and
a unitary, implantable sheath of flexible tubing disposed over at least a portion of the lead body and over at least a portion of each of two or more of the electrodes, wherein the sheath is made from biocompatible, biodegradable material, wherein the sheath has biodegradable adhesive configured and arranged for contacting tissue and adhering the lead to the tissue when the lead is implanted.

11. The implantable medical lead of claim 10, wherein the sheath has electrode windows spaced along the sheath to expose at least one electrode contact of the electrode array.

12. The implantable medical lead of claim 10, wherein the biodegradable material of the sheath is a biodegradable mesh.

13. The implantable medical lead of claim 10, wherein the sheath allows passage of current therethrough to surrounding tissue.

14. The implantable medical lead of claim 10, wherein each of the electrodes is a ring electrode contact.

15. The implantable medical lead of claim 10, wherein the sheath is disposed over at least a portion of each of the electrodes.

16. The implantable medical lead of claim 10, wherein the sheath is disposed completely over all of the electrodes.

17. An implantable neurostimulator lead comprising:
a lead body with a proximal end, a distal end, and a tip at the distal end of the lead body;
a plurality of spaced-apart electrodes disposed along the distal end of the lead body, the electrodes configured and arranged for providing electrostimulation to surrounding tissue when the lead is implanted; and
an implantable sheath disposed over at least a portion of the lead body and over at least a portion of each of two or more of the electrodes, wherein the sheath is slidably removable from the lead body after implantation, wherein the sheath has biodegradable adhesive configured and arranged for contacting tissue and adhering the lead to the tissue when the lead is implanted.

18. The neurostimulator lead of claim 17, wherein the sheath comprises a flexible tubing.

19. The neurostimulator lead of claim 17, wherein the sheath is removable from the lead body and array of electrodes leaving the sheath substantially intact.

20. The neurostimulator lead of claim 17, wherein the sheath is unitary and comprises a plurality of windows aligned with the two or more of the electrodes over which the sheath is disposed.

21. An implantable medical lead comprising:
a lead body with a proximal end, a distal end, and a tip at the distal end of the lead body;
an array comprising spaced-apart electrodes disposed along the distal end of the lead body;
and
a unitary, implantable sheath of flexible tubing disposed over at least a portion of the lead body and over at least a portion of each of two or more of the electrodes, wherein the sheath is removable from the lead body and array of electrodes after implantation of the medical lead, leaving the sheath substantially intact, wherein the sheath has biodegradable adhesive configured and arranged for contacting tissue and adhering the lead to the tissue when the lead is implanted.

22. An implantable medical lead comprising:
a lead body with a proximal end, a distal end, and a tip at the distal end of the lead body;
an array comprising spaced-apart electrodes disposed along the distal end of the lead body;
and
a unitary, implantable sheath of flexible tubing disposed over at least a portion of the lead body and over at least a portion of each of two or more of the electrodes, wherein the sheath is slidably removable from the lead body after implantation, wherein the sheath has biodegradable adhesive configured and arranged for contacting tissue and adhering the lead to the tissue when the lead is implanted.

23. An implantable medical lead comprising:
a lead body with a proximal end, a distal end, and a tip at the distal end of the lead body;
an array comprising spaced-apart electrodes disposed along the distal end of the lead body;
and
a unitary, implantable sheath of flexible tubing disposed over at least a portion of the lead body and over at least a portion of each of two or more of the electrodes, wherein the lead is configured and arranged to allow removal of the lead body and array of electrodes from the sheath, when the lead is implanted in a patient body, leaving the sheath in the patient body, wherein the sheath has biodegradable adhesive configured and arranged for contacting tissue and adhering the lead to the tissue when the lead is implanted.

* * * * *